US00PP07793P

United States Patent [19]

Drewlow

[11] Patent Number: Plant 7,793

[45] Date of Patent: Feb. 18, 1992

[54] IMPATIENS PLANT NAMED BLAZON

[75] Inventor: Lyndon W. Drewlow, Ashtabula, Ohio

[73] Assignee: Mikkelsens, Inc., Ashtabula, Ohio

[21] Appl. No.: 607,376

[22] Filed: Oct. 31, 1990

[51] Int. Cl.[5] ..... A01H 5/00
[52] U.S. Cl. ..... Plt./68
[58] Field of Search ..... Plt./68

*Primary Examiner*—James R. Feyrer

*Attorney, Agent, or Firm*—Foley & Lardner

[57] ABSTRACT

A new and distinct cultivar of Impatiens plant named Blazon, characterized by its large, deep crimson red flowers, highly self-branching habit, large dark green leaves which have a slightly reddish cast to midrib and green venation on leaf underside, early blooming and floriferous habit, two flowers per leaf axil, and its ability to continuously flower under high sunlight, and high as well as cool temperatures.

1 Drawing Sheet

The present invention comprises a new and distinctive cultivar of Impatiens plant, botanically known as Impatiens, and referred to by the cultivar name Blazon. Blazon was developed by me through controlled breeding by crossing Mirach, disclosed in U.S. Plant Pat. No. 6,309 (seed parent) with Mikkelsen Seedling No. 85-185-1 (pollen parent).

Asexual reproduction by terminal or stem cuttings has shown that the unique features of this new impatiens are stabilized and are reproduced true to type in successive propagations.

The following combination of characteristics distinguish Blazon from both its parent varieties and other cultivated impatiens of this type known and used in the floriculture industry. Characteristics are described with reference to the comparison cultivars Red Planet, disclosed in U.S. Plant Pat. No. 4,690, and the seed or female parent Mirach. Color references are to the Royal Horticultural Society Colour Chart (R.H.S.).

1. Blazon has deep crimson red (45A) flowers which are redder than Red Planet (46B) and Mirach (42A).

2. The flower diameter of Blazon is 6.0 to 6.5 cm, while the flower diameter of both Red Planet and Mirach are 5.0 to 5.5 cm.

3. Blazon has a semi-upright, more self-branched growth habit than Red Planet and Mirach, both of which have a mounded, less branched growth habit.

4. The leaves of Blazon and Red Planet are dark green, while the leaves of Mirach are slightly lighter green. All have similar cream variegation around the midrib but Blazon has the least amount of variegation.

5. The leaves of Blazon are larger (12–15 cm long and 4–5 cm wide) than either Mirach (9–10 cm long and 2.5 to 3.5 cm wide) or Red Planet (10 cm long and 3 cm wide).

6. Blazon has a slightly reddish cast to the midrib of the leaf, similar to Mirach, with Red Planet having more red coloration in the midrib.

7. Blazon and Mirach have green venation on the underside of the leaf, whereas Red Planet has red venation.

8. Blazon is from 7 to 10 days earlier to bloom than Red Planet, and similar to Mirach. Moreover, the flowers are longer lasting than the flowers of either Mirach or Red Planet.

9. The spurs of the flowers of Blazon have a green tip, similar to Mirach, while Red Planet has a reddish purple tip.

10. Most leaf axils of Blazon have two flower buds, while Mirach has fewer leaf axils with two flowers and Red Planet has only one flower bud per leaf axil.

The accompanying colored photograph is a front perspective view illustrating the overall appearance of Blazon and showing the colors as true as reasonably possible to obtain in a colored reproduction of this type. The photograph was taken in March 1990 under natural light on an overcast day under double poly greenhouse covering at Ashtabula, Ohio.

The following is a detailed description of Blazon, based on plants produced in greenhouses in Ashtabula, Ohio during the summer season of the year. Plants were grown in 15 cm pots and measurements were taken 16 weeks after rooted cuttings were planted. Height measurements were taken from the soil line of the container. The plants were grown at 65°–68° F. night temperatures, under 3500 to 4500 foot candles of light, and 240 ppm nitrogen, 240 ppm potassium, and 175 ppm phosphorous nutritional levels with trace elements added. Habit of growth, foliage coloration, leaf variegation, size of leaves and flower size will be greatly influenced by nutritional and environmental conditions. Color references are made to the Royal Horticultural Society Colour Chart (R.H.S.) except where general terms of ordinary dictionary significance are used.

Parentage: A controlled cross between female parent Mirach and male parent Mikkelsen Seedling No. 85-185-1.

Propagation:

A. *Type cutting.*—Stem 15 mm long will develop to 4 to 5 cm long in 18 to 21 days.

B. *Time to initiate roots.*—8–10 days at 23° C. summer; 10–12 days at 20° C. winter.

C. *Rooting habit.*—Heavy, fibrous.

Plant description: Habit of growth, foliage coloration and size of leaf will be greatly influenced by nutritional and environmental conditions. Thus, data that follows was taken from plants grown under the conditions stated above.

A. *Form and habit of growth.*—Semi-upright; self-branched; intermediate in height; vigorous growing, continuous flowering herb with flowers over the top of foliage.

B. *Foliage description.*—Dark green leaves with cream colored midrib, green venation on under side of the leaves, and a trace of cream variegation around midrib on lower half of the leaf. 1. Size: 12 to 15 cm long and 4 to 5 cm wide at maturity. 2. Shape: Lanceolate with acuminate apex and acute base. 3. Texture: Both upper and lower surfaces are glabrous. 4. Margin: Slightly serrated with fine ciliate. 5. Color: Young foliage top side, 146A; under side 146B. Mature foliage top side 147A; under side 147B. 6. Venation: Pinnate; green in color.

Flowering description:

A. *Flowering habits.*—Flowers continuously from leaf whorl in a progressively orderly manner, usually with two flowers per leaf axil. All first flowers in a whorl open before the second flower in the leaf axil of that whorl starts to open. When second flowers of a leaf axil start to open, the first flowers of the leaf axils of the whorl above start to open. It takes 5 to 7 days for a mature bud to fully open, with the flowers lasting two weeks or longer depending on the environment.

B. *Natural flowering season.*—Indeterminant and continuous. Quantity of flowering increases with increasing levels of light.

C. *Flower buds.*—Ellipsoidal, flowers perfect. Bright red spur up to 4.5 cm long with green tip on a mature bud, with the throat behind the ovary and originating from the major sepal.

D. *Flowers borne.*—Individual reddish pedicels (3 cm long) from a whorl of 5 to 6 leaves flowering progressively around the whorl as buds and leaves develop. Most leaf axils have two flowers.

E. *Quantity of flowers.*—Very floriferous. Because of long lasting flowers and two flowers per leaf axil, flowers frequently open at three whorls at once. Flower development is continuous and is above leaf canopy.

F. *Diameter of flower.*—6.0 to 6.5 cm.

G. *Petals.*—1. Shape: Heart-shaped; two lower petals are larger than other three. 2. Color: Top side when opening slightly deeper than 45A, fading to 45B. Under side 46B. 3. Number of petals: Five. 4. Size of petals: Standard — 4.0 cm wide by 3.2 cm long; two equal lobes, shallow cut. Wings — 2.5 cm wide by 3.5 cm long; two unequal lobes, shallow cut. Keel — 3.5 cm wide by 4.5 cm long; two unequal lobes, deep cut.

Reproductive organs:

1. *Stamens.*—Five in number. Anther shape is hooded; cream in color with red tinge; pollen color is cream.

2. *Pistils.*—Stigma shape is five segmented column; cream colored. Style color is cream. Ovaries, five in number; 5 mm in size; color is bright green.

Disease resistance: No significant disease and insect problems to date. Blazon is much more tolerant to the disease Rhizoctonia than Mirach.

OTHER IMPORTANT CHARACTERISTICS

1. Blazon has larger diameter stems than either Mirach or Red Planet and is therefore better able to hold up to its large flowers.

2. Blazon has shown the ability to tolerate both high temperatures and high sunlight levels, as well as cool temperatures (40°-50° F.). Thus, the growing season can be extended.

3. Self-branching, early flowering nature allows Blazon to be grown in 10 cm pot. However, Blazon is also vigorous so that it can also be grown in 15 to 25 cm containers.

I claim:

1. A new and distinct cultivar of Impatiens plant named Blazon, as illustrated and described.

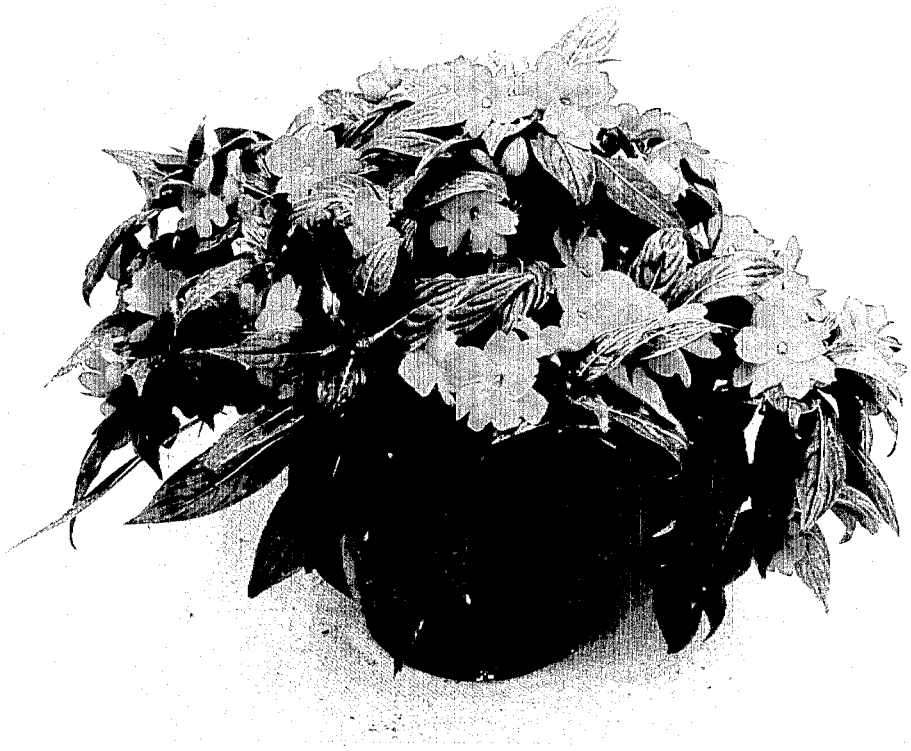

* * * * *